United States Patent [19]
Galloway

[11] Patent Number: 5,343,900
[45] Date of Patent: Sep. 6, 1994

[54] NEEDLE BUNDLE DRIVER AND METHODS

[75] Inventor: Edwin J. Galloway, Menasha, Wis.

[73] Assignee: Galloway Company, Neenah, Wis.

[21] Appl. No.: 63,550

[22] Filed: May 18, 1993

Related U.S. Application Data

[60] Continuation-in-part of Ser. No. 39,748, Mar. 30, 1993, Pat. No. 5,269,350, which is a division of Ser. No. 787,545, Nov. 4, 1991, Pat. No. 5,199,473, which is a division of Ser. No. 543,747, Jul. 11, 1990, Pat. No. 5,086,813, which is a division of Ser. No. 261,020, Oct. 20, 1988, Pat. No. 4,941,517.

[51] Int. Cl.⁵ ............................................ B65D 41/20
[52] U.S. Cl. .................................... 141/1; 141/98; 141/312; 141/319; 141/329; 141/365; 141/369; 604/411; 604/905; 206/219; 269/909
[58] Field of Search ............. 141/1, 98, 312, 319–322, 141/363–366, 320, 369, 367, 329, 330; 604/403, 407, 411–416, 905; 206/219; 215/247, 241; 74/813 R; 269/63, 55, 909, 329

[56] References Cited

U.S. PATENT DOCUMENTS

| | | | |
|---|---|---|---|
| 2,608,972 | 9/1952 | Chrigstrom | 215/247 X |
| 2,767,587 | 10/1956 | Perkins | 73/421.5 |
| 2,911,123 | 11/1959 | Saccomanno | 215/247 |
| 2,994,224 | 8/1961 | Brown | 73/422 |
| 3,238,784 | 11/1968 | Dorsey et al. | 73/425 |
| 3,412,613 | 11/1968 | Brown et al. | 73/425.2 |
| 3,460,702 | 8/1969 | Andrews | 215/247 |
| 3,682,315 | 8/1972 | Haller | 604/415 X |
| 3,707,239 | 12/1973 | Harris, Sr. et al. | 215/247 |
| 3,779,082 | 12/1973 | Galloway | 141/330 |
| 3,900,028 | 8/1973 | McPhee | 604/415 |
| 3,930,413 | 1/1976 | Laird et al. | 73/421 |
| 4,084,718 | 4/1978 | Wadsworth | 215/247 |
| 4,296,759 | 10/1981 | Joslin | 604/413 |
| 4,359,908 | 11/1982 | Perras | 73/863.85 |
| 4,423,641 | 1/1984 | Ottung | 73/863.86 |
| 4,445,896 | 5/1984 | Gianturco | 604/415 |
| 4,580,453 | 4/1986 | Taylor | 73/863.86 |
| 4,676,788 | 6/1987 | Vincent | 604/415 |
| 4,941,517 | 7/1990 | Galloway | 141/1 |
| 5,086,813 | 2/1992 | Galloway | 141/1 |
| 5,199,473 | 4/1993 | Galloway | 141/312 |
| 5,269,350 | 12/1993 | Galloway | 141/1 |

*Primary Examiner*—Ernest G. Cusick
*Attorney, Agent, or Firm*—Thomas D. Wilhelm

[57] ABSTRACT

This invention provides apparatus and methods for aseptically transferring fluid into or out of a closed aseptic processing system. The apparatus comprises a novel fluid transfer station, including a needle bundle driver, a mounting base mounting the driver to a tank, and a fluid receiver assembly. The needle bundle driver includes a needle bundle holder which holds a needle bundle while the ends of the needles are driven into the tank through the fluid receiver assembly. The cooperation between the needle holder and the needle bundle includes a pair of clamp arms which extend outwardly from the needle bundle, and terminate in top and bottom pods. The top and bottom pods cooperate with the top surface of a support block and a bottom surface with an overhead clamping block, for locking the needle bundle into the needle holder, immobilizing the needle bundle between the clamping block and the support block. With the needle bundle thus immobilized, the needle bundle is driven toward the tank, driving the ends of the needles through the plug and into the tank, thereby establishing fluid communication through the needles, between the needle holder and the tank. Fluid is then passed through the needles and into or out of the tank.

24 Claims, 7 Drawing Sheets

NEEDLE BUNDLE DRIVER AND METHODS

This application is a continuation in part of U.S. application Ser. No. 08/039,748, filed Mar. 30, 1993, U.S. Pat. No. 5,269,350; which is a division of U.S. application Ser. No. 07/787,545 filed Nov. 4, 1991, now U.S. Pat. No. 5,199,473; which is a division of U.S. application Ser. No. 07/543,747 filed Jun. 7, 1990, now U.S. Pat. No. 5,086,813; which is a division of U.S. application Ser. No. 07/261,020 filed Oct. 20, 1988, now U.S. Pat. No. 4,941,517; all the above being herein incorporated by reference in their entireties.

FIELD OF THE INVENTION

This application relates to aseptic processing systems, and associated apparatus and methods used for transferring fluid into, or out of, an enclosure such as a tank, a pipe, or other type of enclosure vessel. The invention pertains, for example, to transferring fluids into processing systems which are sensitive to contamination from the outside environment.

BACKGROUND OF THE INVENTION

Hereinafter, the invention is described with respect to its application to processing of dairy products. It is contemplated that both the apparatus and the methods of the invention have application to a wide variety of industrial processes which require transferring of fluid components without introducing contaminating material into the processing enclosure. Thus, the disclosure of dairy processing herein is only illustrative, and is not limiting; whereby a variety of other processing industries are contemplated.

In the processing of dairy products, it is sometimes advantageous to add fluid to the closed aseptic processing system without introducing microbiological or other contamination into the processing system, or similarly to remove fluid from the closed aseptic processing system.

Some processors of dairy products have addressed this problem by attempting to keep sterile the rooms in which the processing takes place. Under the assumption that sterility is achieved, fluid is transferred into or out of the processing system through an open port in e.g. a tank. Keeping the room sterile is difficult; and the sterile room practice is, of course, expensive.

Other processors have addressed this problem of attempting aseptic transfer by attempting to control the amount of microbiological organisms immediately around the open port, as by using a fire ring around the open port. With the fire ring, it is contemplated that microbiological organisms in the vicinity of the open port are destroyed by the heat of the fire.

Still another known method of addressing aseptic transfer is to use a steam ring in place of the fire ring.

Another problem in the dairy processing industry is that the valves and pumps typically used to transfer, for example processed material from one tank to another are difficult to keep clean and sanitized. So special techniques, such as steam tracing, steam jacketing and the like of pumps and valves, have been developed to assure maintenance of aseptic conditions.

These steam-related procedures are time consuming and expensive, requiring a high level of training and skill on the part of the operators. Such complex procedures carry the usual risk of human error. Further, the high temperature inherent in steam creates a risk of the operators being burned. Finally, the heat brought into the plant by the steam must be removed by air conditioning. This adds to the overall cost of air conditioning the plant to maintain specified ambient plant conditions.

In my prior applications and patents mentioned above, from which this application depends, I disclose an aseptic fluid transfer system comprehending an aseptic plug, mounted into the tank wall. The plug is held temporarily mounted to and extending through the tank wall, by a metal tank adapter which is permanently welded into the tank wall, as taught in, for example my U.S. Pat. No. 4,941,517. An hypodermic or like needle can penetrate the plug, whereby the end of the needle protrudes into the interior of the tank. This establishes an aseptic penetration into the tank, whereupon fluid can be passed into or out of the tank, through the needle.

To transfer a larger quantity of fluid, a plurality of needles can be arranged in a needle bundle, with the needles arrayed in a pattern corresponding to the pattern of needle channels which extend through the plug. All the needles, as part of the needle bundle, should be pushed into the plug in the same operation whereby the ends of all the needles are ultimately disposed in the tank. Fluid is typically passed through all the needles in the needle bundle. The number of needles in the needle bundle thus determines in part the fluid flow capacity of the needle bundle.

In using a single needle to penetrate the plug, the operator selects an unused channel in the plug, aligns the needle with the channel, and pushes the end of the needle through the plug and into the tank.

When using a plurality of needles simultaneously as in e.g. a needle bundle, alignment of the needles, and pushing the plurality of ends of the needles through the plug is more difficult. Alignment is more complicated because all of the needles must be simultaneously aligned with respective channels. Pushing the needle ends through the plug is more difficult because the force required is proportional to the number of needles used, such that a person may not, without mechanical assistance, be able to push hard enough to make the needle ends penetrate into the tank.

It is an object of this invention to provide a fluid transfer station at a tank, the fluid transfer station including a needle bundle driver assembly, a mounting base on the tank, and a plug, the fluid transfer station being adapted to provide indexing of the needle bundle and the plug, and mechanical power to thereby drive a plurality of needle ends through the plug.

It is another object to provide a needle bundle adapted to be driven as part of the needle bundle driver assembly.

It is yet another object to provide a needle bundle holder to hold the needle bundle while the ends of the needles are driven through the plug and into the tank.

It is still another object to provide methods of simultaneously driving a plurality of needle ends through the plug and into the tank.

Another object of the invention is to provide methods of aseptically adding fluid to a processing system, or removing fluid therefrom, using a plurality of needles as the conduits of fluid transfer. Finally, it is an object to provide methods of aseptically transferring fluids into, or out of, a plurality of tanks using a single needle bundle driver assembly.

SUMMARY OF THE DISCLOSURE

Some of the objects are attained in a needle bundle driver, adapted to drive needles in a bundle through an aseptic tank plug, such that ends of the needles project into the tank. Thus, the needles provide aseptic fluid communication between the inner and outer surfaces of the tank.

The needle bundle driver comprises a tank bracket adapted to mount the needle bundle driver adjacent the tank, the tank bracket having a first end defined by a first end plate, adapted to face toward the tank, a second end defined by a second end plate, adapted to face away from the tank, and a length extending between the first and second ends; a needle bundle holder; and a power ram; both the needle bundle holder and the power ram being mounted to the tank bracket.

The needle bundle holder is moveable along the length of the tank bracket, toward and away from the first end of the tank bracket. The needle bundle holder comprises a support block, having first and second ends disposed respectively toward the first and second ends of the tank bracket, a top, and a recess, preferably a channel in the top, the preferred channel having a length extending in a direction between the first and second ends of the support block; and a lock arm, having first and second ends disposed toward the first and second ends respectively of the support block, the lock arm being mounted above the support block by a web, mounting the lock arm for angular movement with respect to the first end of the support block. Thus, the second end of the lock arm can be raised or lowered while the first end remains at a relatively constant height above the support block.

An upper lock on the needle bundle holder is adapted to lock the second end of the lock arm in a raised position. A lower lock is adapted to lock the second end of the lock arm in a lowered position. A clamping block is mounted to the lock arm.

The power ram is adapted to move the needle bundle holder toward, and away from, the first end of the tank bracket.

Preferably, the web comprises a spring, with the spring having a rest position wherein the second end of the lock arm is disposed between the recited raised position and the recited lowered position.

In preferred embodiments, the clamping block is slidably mounted to the lock arm, such that the clamping block can slide, along the lock arm, toward and away from the first end of the lock arm. The lock arm is preferably received in a slot in the clamping block whereby the slot and the lock arm are engaged to effect the sliding of the lock arm with respect to the clamping block, the lock arm having a plurality of grooves, at least 0.25 millimeter deep, extending across the direction of sliding of the clamping block such that the grooves pass through the slot in the clamping block as the clamping block slides with respect to the lock arm.

As illustrated herein, the clamping block preferably has an arcuate face disposed toward the support block.

The channel in the support block preferably also has a plurality of grooves, again at least 0.25 millimeter deep, extending across its length.

Other objects of the invention are achieved in a needle bundle assembly, comprising a needle holder, having first and second ends; a plurality of needles extending from the first end of the needle holder, the needles being arranged, as an array, in a pattern; a sheath, having a first end disposed away from the needle holder and a second end disposed toward the needle holder, needle guides extending through the sheath, between the first and second ends of the sheath, the needle guides being arranged in the same pattern as the needles whereby the needles can extend through the needle guides, the sheath being disposed over the ends of the needles; and a spring disposed between the needle holder and the sheath. The spring positions the sheath such that the ends of the needles are disposed in the sheath.

With the needles extending along a longitudinal axis of the needle bundle assembly, the needle holder preferably comprises a pair of clamp arms extending outwardly, in a direction transverse to the longitudinal axis, and top and bottom pods on the ends of respective ones of the clamp arms, the top and bottom pods having respective ends which are arcuate.

The needle bundle assembly preferably includes a sleeve which is impermeable to microbiological organisms, extending between the needle holder and the sheath, and around the array of needles; such that the sleeve protects the needles from microbiological invasion between the needle holder and the sheath. A tape, impermeable to microbiological organisms, covers the needle guides on the first end of the sheath, whereby the combination of the sleeve and the tape are effective to protect the needles from microbiological invasion between the first end of the needle holder and the ends of the needles in the sheath.

The invention also contemplates a needle bundle driver assembly, comprising a needle bundle driver and a needle bundle, both as described above, the needle bundle being securely held in the needle bundle driver, preferably by the top and bottom pods being engaged with, and clamped between the clamping block and the support block.

Preferably, the clamping block has an arcuate face generally corresponding in shape with the end of the top pod, and the support block has a channel generally corresponding, in a direction transverse to the longitudinal axis, with the shape of the end of the bottom pod.

The apparatus of the invention further comprehends an aseptic transfer system including a needle bundle driver assembly and an aseptic plug, mounted in a tank wall, such that the system is adapted to accommodate aseptic penetration of needles through the plug to thereby facilitate aseptic fluid communication into the tank through the needles. The plug and the sheath have cooperating index guides which cooperate with each other only when the needles in the needle bundle are both laterally and rotationally aligned with corresponding needle channels in the plug.

The invention comprehends a method of driving needles aseptically into a closed tank. The method comprises the steps of mounting a needle bundle in a needle bundle driver, to make a needle bundle driver assembly, as described above; engaging an index guide on the needle bundle with a cooperating index guide on a plug in a wall of the tank; immobilizing the needle bundle in the needle bundle driver; and driving the needle bundle assembly toward the tank, whereby the ends of the needles pass through the plug and into the tank, thereby establishing fluid communication with the interior of the tank.

Preferably, after the needle bundle is immobilized in the needle bundle driver, and before the needle bundle is driven, an aseptic fluid carrier, such as a hose, pipe, or other tubing, is connected to the second end of the needle holder, to provide fluid carrying capacity at the needle bundle. The method contemplates, with fluid communication established, passing fluid through the needles between the aseptic fluid carrier and the closed tank.

DETAILED DESCRIPTION OF THE ILLUSTRATED EMBODIMENTS

Figure 1:
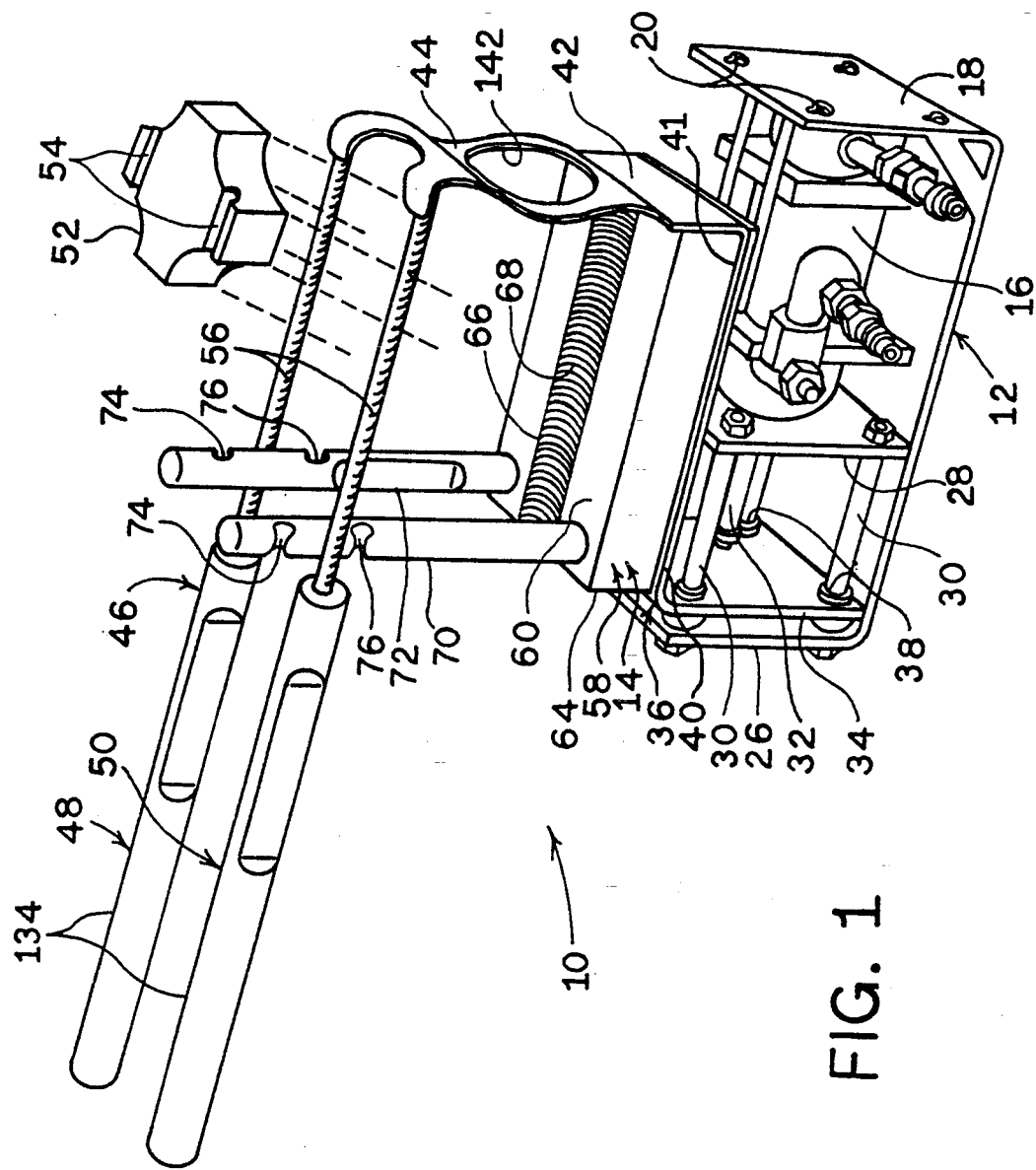
FIG. 1 is a pictorial view of a needle bundle driver of the invention, with the clamping block displaced, and the lock arm at rest between the upper lock position and the lower lock position.

Referring, now to the drawings, FIG. 1 shows the needle bundle driver 10, including a tank bracket 12, a needle bundle holder 14, and power ram 16.

Figure 5:
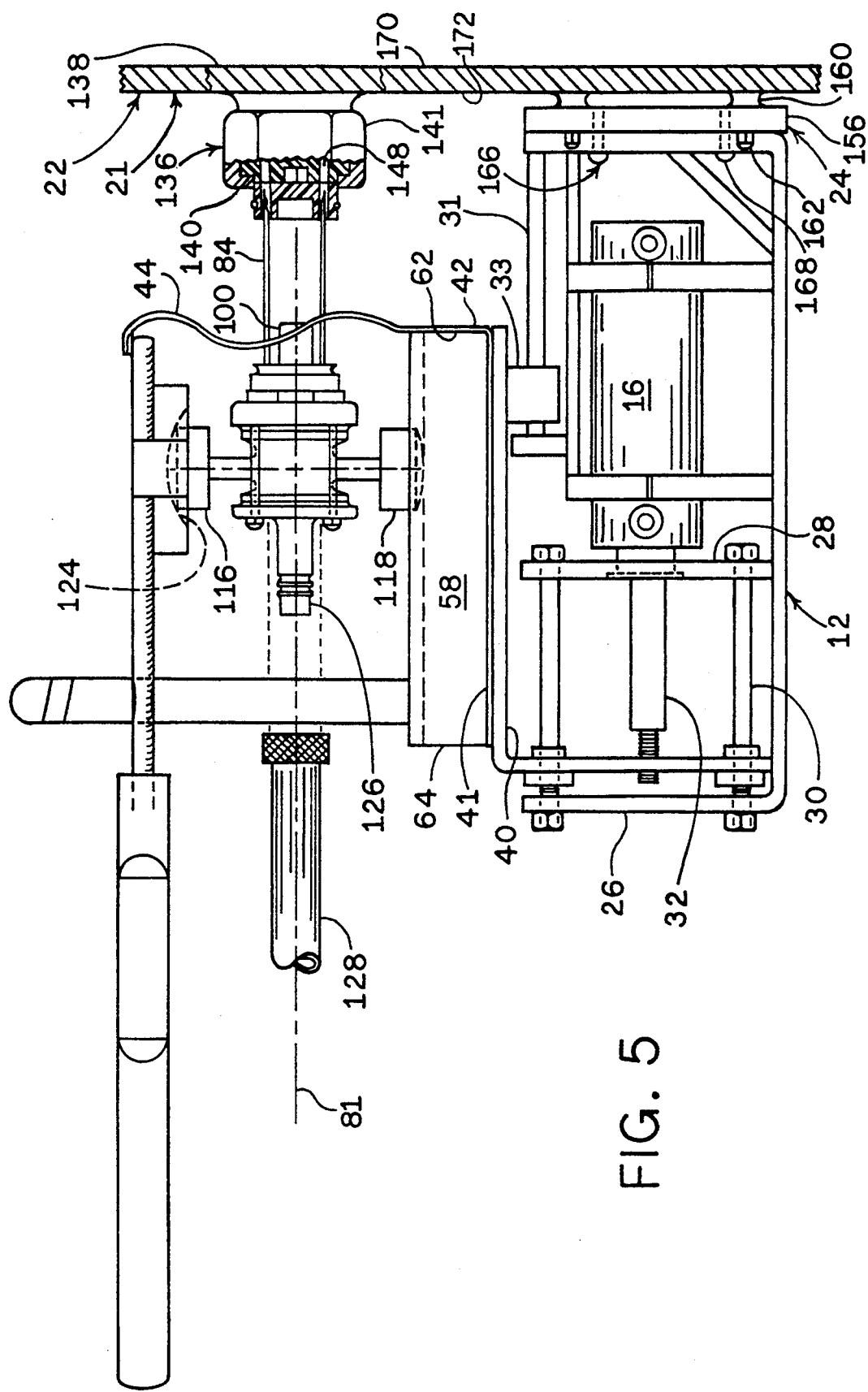
FIG. 5 is a side elevation view, with parts cut away, of the aseptic fluid transfer station, including a mounting base, a needle bundle driver assembly, a needle bundle, and a fluid receiver assembly mounted in a tank wall.
Figure 6:
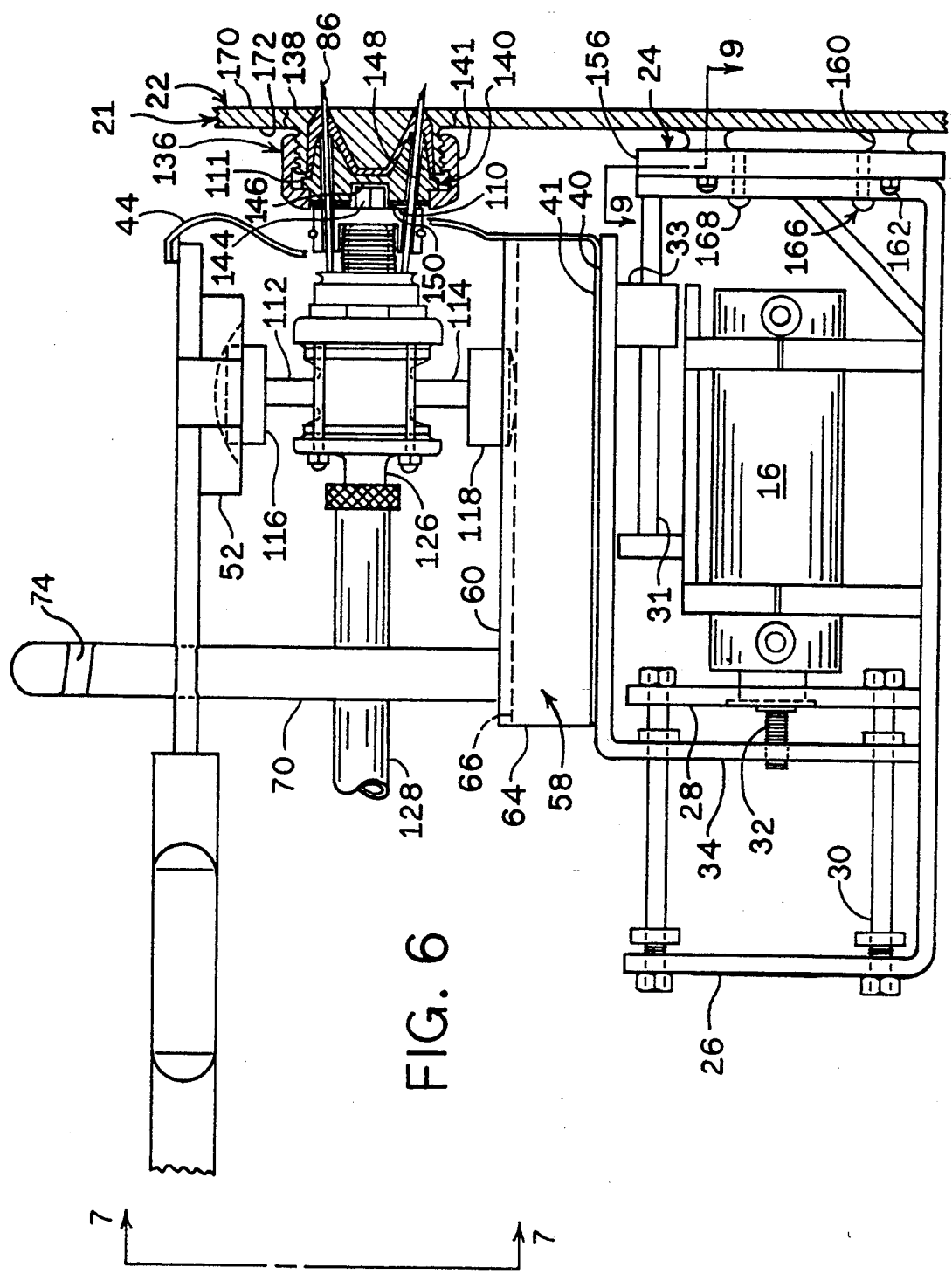
FIG. 6 is a side elevation view as in FIG. 5, with the ends of the needles driven through the plug and into the interior of the tank.
Figure 8:
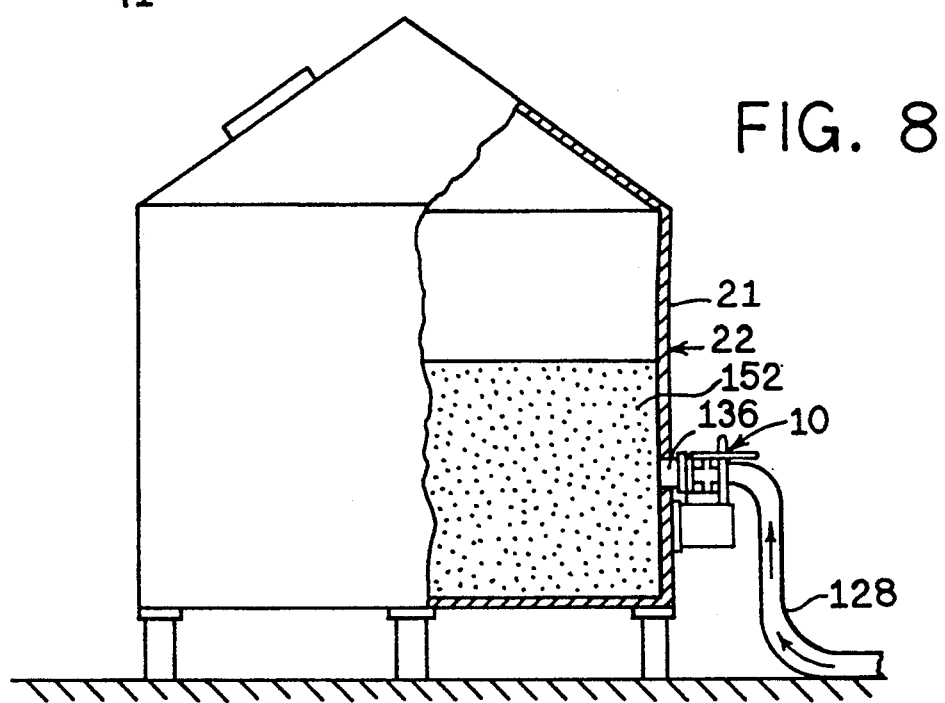
FIG. 8 is a pictorial view, with parts cut away, of a tank using the aseptic transfer system of the invention.

The tank bracket 12 has a first end defined by end plate 18 which is disposed toward wall 21 of the tank 22 (FIGS. 5, 6, and 8). End plate 18 has a plurality of holes 20 which are used to mount the bracket 12 to the tank wall 21 through mounting base 24 (FIGS. 5 and 6).

Tank bracket 12 has a second end defined by end plate 26 which is disposed away from the tank 22 when the needle bundle driver is mounted to the tank. An upstanding middle plate 28 is disposed between end plates 18 and 26. Slide bars 30 are secured to, and extend between end plate 26 and middle plate 28 in a direction generally perpendicular to end plate 18.

Power ram 16 is mounted to tank bracket 12 between end plate 18 and middle plate 28. The ram arm 32 extends through middle plate 28 and is secured to upstanding guide plate 34 of needle bundle holder 14, guide plate 34 being part of the interface 36 joining needle bundle holder 14 and tank bracket 12 to each other. Slide bars 30 extend through corresponding closely-fitting holes 38 in guide plate 34. Similarly, slide bars 31 extend through holes (not shown) in support block 33 which depends from near the opposing end of support plate 40. Thus, when the ram is activated, withdrawing or extending ram arm 32, guide plate 34 is moved toward or away from the ram, with the slide bars 30 sliding respectively with respect to holes 38.

Interface 36 includes guide plate 34 and support plate 40. Upwardly-disposed end plate 42 comprises the end of the holder which is to be disposed toward the tank, and depends from support sheet 41, which is secured to support plate 40.

Figure 2:
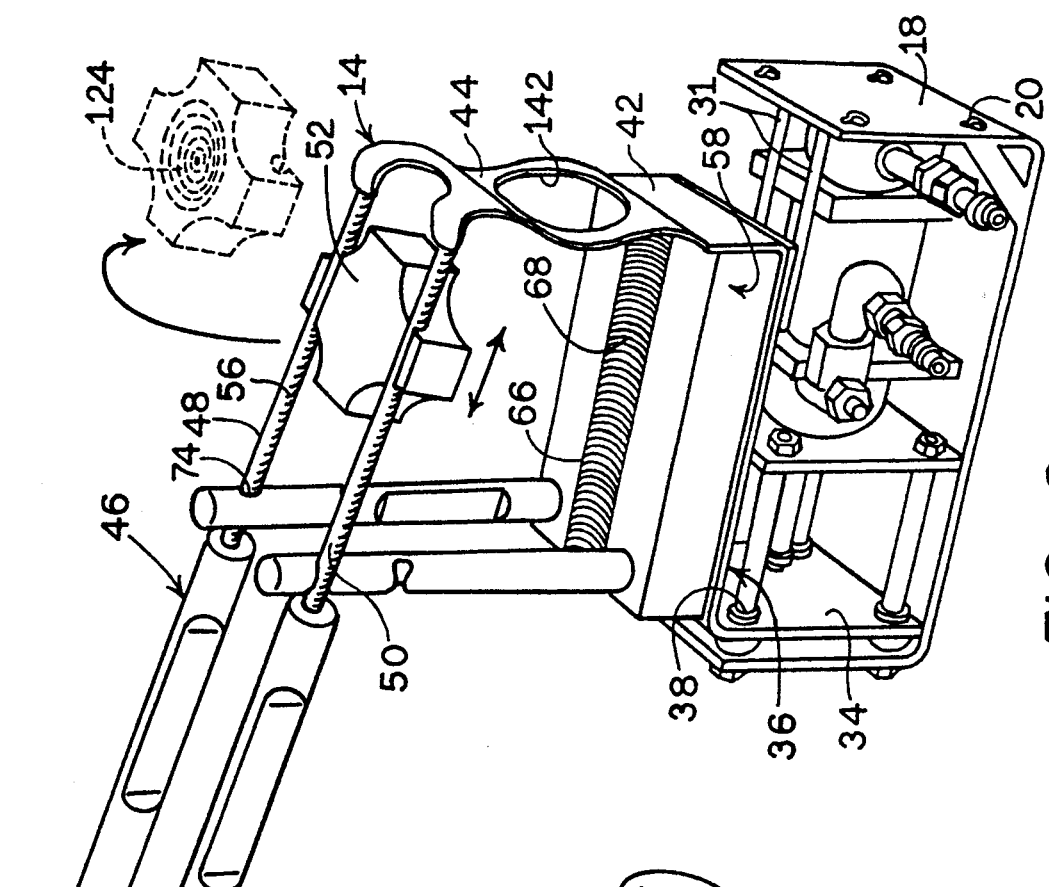
FIG. 2 is a pictorial view as in FIG. 1, with the lock arm in the upper lock position, with the clamping block in place on the lock arm, and secondarily shown upside down in dashed outline.

Biasing leaf spring 44 is a metal web, rigidly secured to end plate 42 and extends upwardly to lock arm 46, which is comprised of handles 48 and 50, and clamping block 52. Clamping block 52 includes slide slots 54 which are resiliently deformable to receive handles 48, 50 as shown in FIG. 2. Slots 54 grip handles 48, 50 tightly enough to prevent free sliding of clamping block 52 on handles 48, 50, while allowing block 52 to slide when so urged with modest manual force. Grooves 56, at least 0.25 millimeter deep, preferably 0.5 mm. deep, extend across handles 48, 50 on those areas of the handles which can be received in slots 54. Grooves 56 increase the holding power that prevents sliding of clamping block 52 with respect to handles 48, 50 under clamping conditions.

Support block 58 of needle bundle holder 14 is secured to support plate 40 of interface 36 through support sheet 41. Support block 58 has a top 60, a first end 62 disposed toward the tank 22 and a second end 64 disposed away from tank 22. Top 60 includes a channel 66 extending from the first end 62 to the second end 64. Channel 66 includes grooves 68 at least 0.25 mm. deep, preferably 0.5 mm. deep, extending in a direction transverse to its length.

A pair of lock rods 70, 72 extend upwardly from support block 58. Each lock rod has an upper lock slot 74, and a lower lock slot 76, for receiving the handles 48, 50 in locking relationship thereto.

Figure 3:
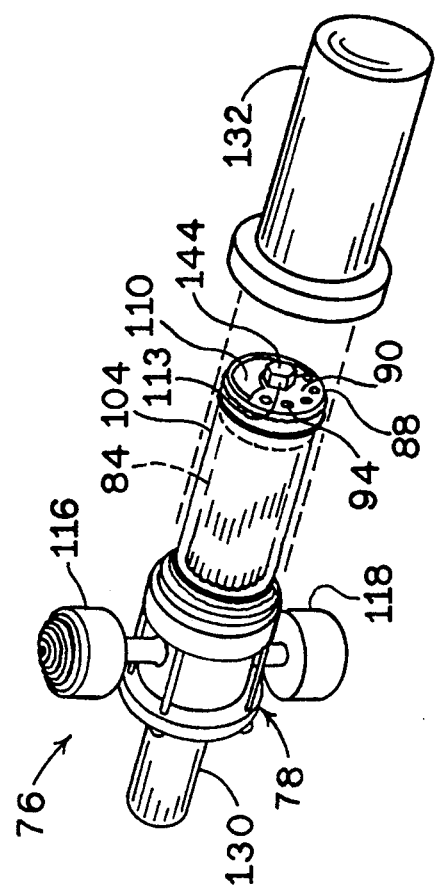
FIG. 3 is a pictorial view, with part cut away, of the needle bundle, with the outer needle cover removed.
Figure 4:
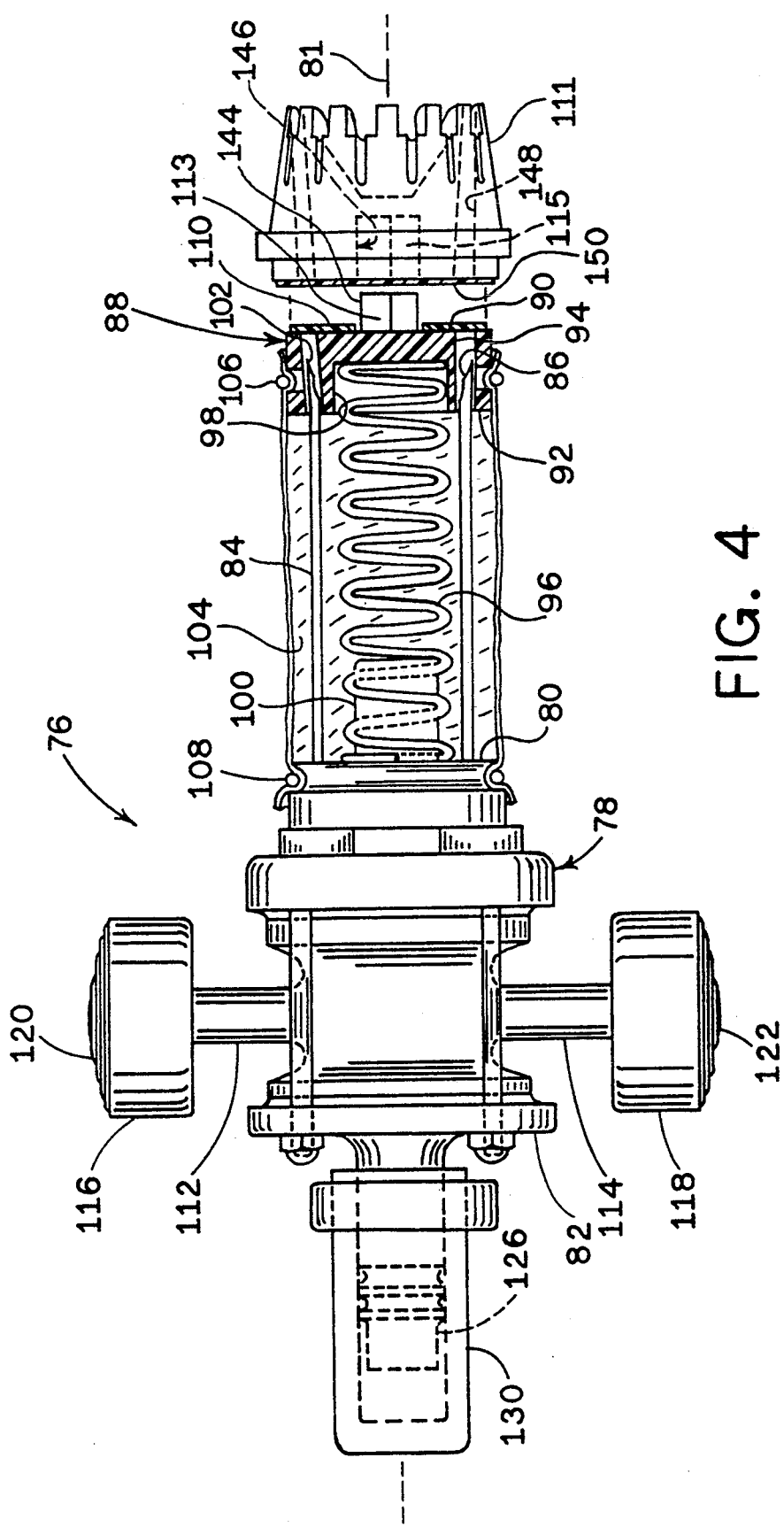
FIG. 4 is a side view of the needle bundle, with parts cut away, and showing the needle bundle aligned with a core of a plug.

Referring to FIGS. 3 and 4, the needle bundle assembly 76 comprises a needle holder 78 having a first end 80, and a second end 82. Needles 84 extend from the first end 80, along longitudinal axis 81, and have ends 86 disposed away from the holder 78, the needles being arranged as an array, in a pattern, illustrated as a circular pattern.

A sheath 88 has ends 90, 92 disposed away from and toward the needle holder respectively. Needle guides 94 extend through the sheath 88 between the ends 90, 92, the guides being arranged in the same pattern as the needles 84. Needle guides 94 receive the ends 86 of the needles. Compression spring 96 extends between the needle holder 78 and cavity 98 in sheath 88. Spring 96 is tightly held in cavity 98 and on stud 100 of the needle holder such that spring 96 serves as a primary mount, mounting sheath 88 to the needle holder, and spacing sheath 88 the proper distance from needle holder 78 such that the needle ends, including tips 102, are received within sheath 88. By enclosing the tips 102 of the needles, sheath 88 protects the tips from being damaged or contaminated, and protects users from being injured by the needles.

A rubber sleeve 104, which is impermeable to microbiological organisms, extends around the outside of the array of needles between needle holder 78 and sheath 88, and is held in place by o-rings 106 and 108. A plastic tape 110, which is impermeable to microbiological organisms, covers the needle guides 94 on an end 90 of sheath 88 which is disposed away from the needle holder. FIG. 3 shows part of the tape 110 cut away to show the pattern of needle guides 94 in the sheath. Thus the combination of sleeve 104 and tape 110 protect the needles, as they extend from the first end 80 of the needle holder 78, from microbiological invasion.

FIG. 4 shows a core member 111 of the plug 140 aligned with the needle bundle assembly. Male index 144 on sheath 88 and female index 146 on core member 111 are sized to cooperatively index with each other. Indexes 144 and 146 have corresponding flat surfaces 113, 115 extending in the direction of axis 81, thus assuring rotational as well as lateral alignment of indexes 144, 146 when they are cooperatively engaged. The cooperative engagement of indexes 144, 146 thus assures both lateral and rotational alignment of the needle guides 94 in sheath 88 with corresponding needle channels 148 in core member 111 of plug 140.

Figure 7:
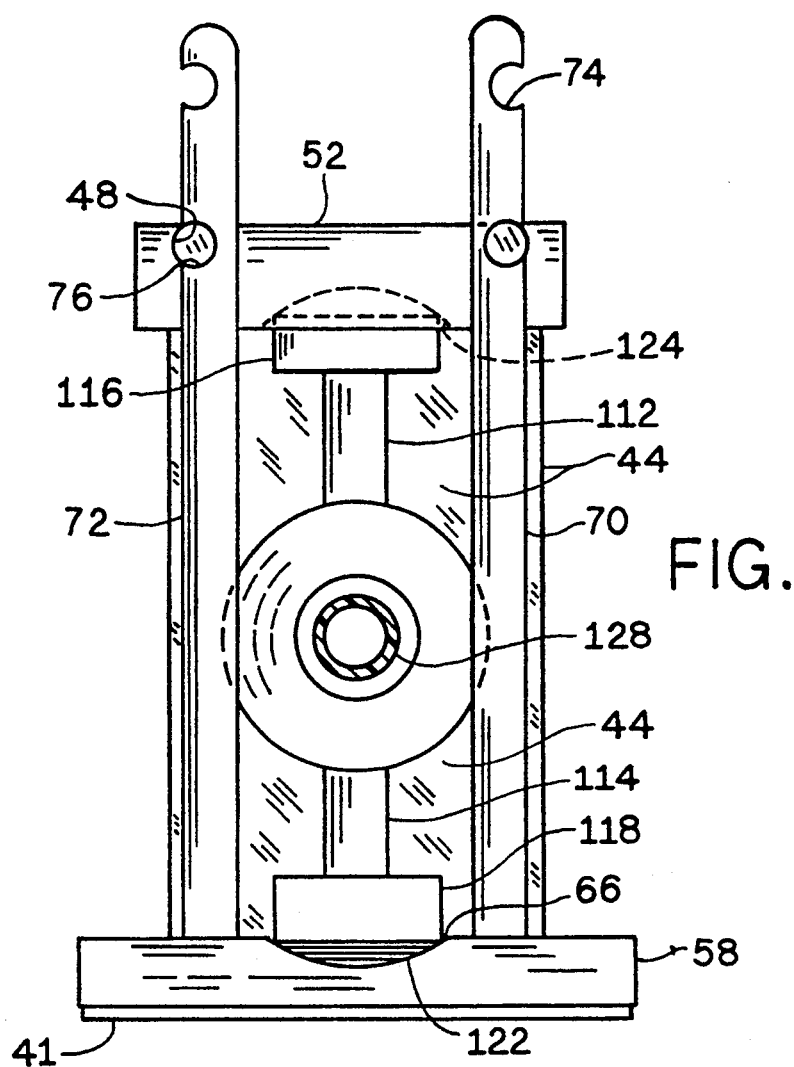
FIG. 7 is a rear elevation taken at 7—7 of FIG. 6, and showing the needle bundle and the needle bundle holder including the support plate and parts above.

A pair of clamp arms 112 and 114 extend outwardly from the needle holder in a direction transverse, preferably perpendicular, to the longitudinal axis 81. Clamp arms 112, 114 terminate at top and bottom pods 116, 118 respectively. Top pod 116 has a convex arcuate top 120. Bottom pod 118 has a convex arcuate bottom 122. Arcuate top 120 corresponds in shape to concave arcuate face 124 in clamping block 52. See FIGS. 2, 5, and 7. Arcuate bottom 122 corresponds in at least one corresponding dimension to the transverse contour of channel 66. See FIG. 7.

The second end 82 of the needle bundle assembly 76 includes a coupling 126 to receive a hose, pipe, or other fluid carrier 128. A rigid cover 130 covers coupling 126 when not in use, protecting it from both physical damage and microbiological invasion. A rigid cover 132 covers the needles 84, rubber sleeve 104, and sheath 88 when the needles are not in use, protecting them from both physical damage and microbiological invasion. Rigid cover 132 also protects against the needles inadvertently puncturing tape 110 and/or a user. Inadvertent puncturing would subject the needles to microbiological contamination. Puncturing a user would, in addition, cause physical injury to the user.

The needle bundle driver is in general made with suitable structural materials such as steel or stainless steel, including tank bracket 12, ram 16, interface 36, leaf spring 44, and handles 48, 50. Support block 58, lock rods 70, 72, clamping block 52, and pods 116 and 118 are made with a hard, but resiliently deformable plastic such as high density polyethylene. Handles 48, 50 may also include plastic grip adapters 134 as shown.

Figure 9:
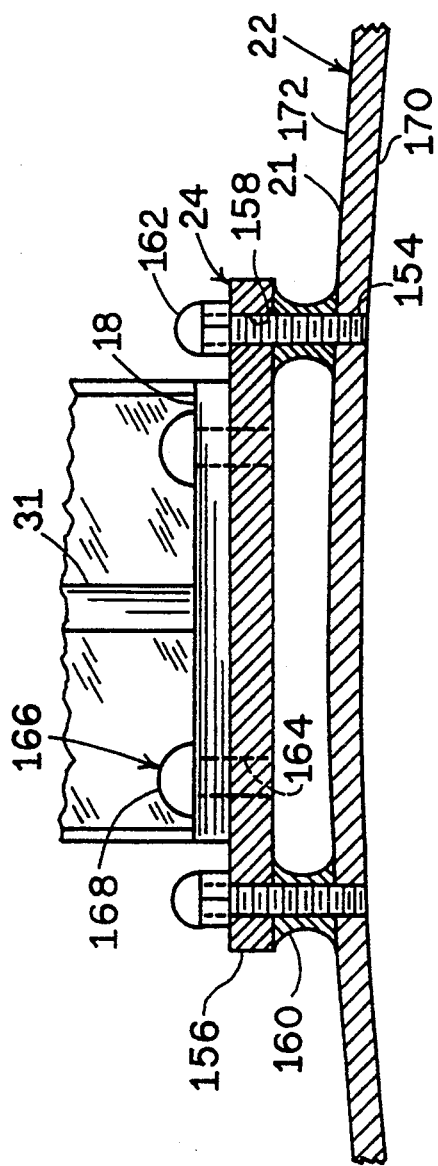
FIG. 9 is a cross section of the mounting base and a fragment of the needle bundle driver, taken at 9—9 of FIG. 5.
Figure 10:
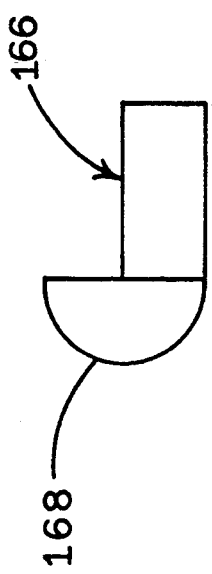
FIG. 10 is a side view of the button head mounting pin.

Referring to FIGS. 9 and 10, mounting base 24 includes a plurality of bolts 154 which are welded into and through the wall 21 of the tank 22. Bolts 154 are appropriately finished on the inside of the tank, in accordance with sanitary or other processing requirements. In the embodiment shown, the bolts are cut off and finished as part of the inner surface 170 of the tank wall 21. Base plate 156 has a plurality of holes 158 having hole size and hole pattern corresponding to the pattern and size of bolts 154, such that bolts 154 fit into holes 158 as shown. Resiliently deformable spacers 160, made of e.g. high density polyethylene, space base plate 156 from the wall 21 of the tank. Base plate 156 is fixedly secured to bolts 154, and thus to the tank wall by cap nuts 162. Holes 164 in base plate 154 generally correspond with the pattern of holes 20 in end plate 18. Button head mounting pins 166 are secured in holes 164 and extend outwardly from base plate 156, to receive end plate 18 between base plate 156 and the button heads 168 of the mounting pins 166.

When a needle bundle driver 10 is mounted on the mounting base 24, and a needle bundle assembly 76 is secured in the needle bundle driver, the needle bundle assembly is aligned with a fluid receiver assembly 136 in the tank wall 21. Fluid receiver assembly 136 comprises a tank adapter 138 permanently welded into the tank wall 21. A removable plug 140, including tape 150 covering its outer surface, is held in the tank adapter 138 by a nut 141. A more detailed description of an illustrative fluid receiver assembly is given in U.S. Pat. No. 4,941,517.

Preparation for use of the apparatus disclosed herein preferably begins with the construction of the tank 22. Preferably, both the bolts 154 and tank adapter 138 are welded into the tank wall 21 when the tank is built. As an alternative, either or both of these elements can be added later as a modification of the tank wall.

As part of the preparation for using the tank 22 in a fluid transfer operation, plug 140 is placed in the tank adapter 138, and secured in the adapter with nut 141. The joining together of the elements of the fluid receiver assembly is thus complete. A dust cover, not shown, is then placed over the entire fluid receiver assembly 136. The tank 22 and the inner surface of the plug 140, which projects into the tank, are then sanitized together.

Also in preparation for using tank 22 in a fluid transfer operation, a base plate 156 is mounted on bolts 154, along with spacers 160, and is secured in place with cap nuts 162. Base plate 156 includes button head mounting pins 166 which have previously been fixedly mounted in holes 164.

Next, the needle bundle driver 10 is mounted to mounting base 24 by engaging holes 20 in end plate 18 over button pin heads 168 such that heads 168 engage end plate 18 in the surface areas of the plate which border holes 20. The needle bundle holder 14 is then positioned away from the tank 22, if not already so positioned, as shown in FIGS. 1 and 2 by extending ram arm 32.

Starting from the rest position shown in FIG. 1, clamping block 52 is assembled to the handles 48, 50 by urging slots 54 around the handles 48, 50 such that the slots 54 resiliently deform and receive the handles as shown in FIG. 2. Clamping block 52 and handles 48, 50, when so assembled, comprise lock arm 46. After assembly to handles 48, 50, clamping block 52 can readily be slid, on the handles, toward and away from leaf spring 44.

With the lock arm thus assembled, lock arm 46 is raised, and handles 48, 50 are locked in the upper lock slots 74 as shown in FIG. 2. As lock arm 46 is raised, spring 44 is flexed, creating a downward bias on lock arm 46 such that the handles 48, 50 are being urged downwardly by spring 44 while they are locked in upper lock slots 74.

The combination of the mounting base 24, the fluid receiver assembly 136, and the needle bundle driver 10, as so assembled, comprise a fluid transfer station, ready to receive the needle bundle assembly 76 and the fluid carrier 128.

With the handles 48, 50 locked in upper lock slots 74, a needle bundle is then mounted in the needle bundle holder 14, and engaged with the fluid receiver assembly 136 as follows. First the dust cover is removed from the fluid receiver assembly, and the outer surface (e.g. tape 150) of the fluid receiver assembly is sanitized as by wiping it with an alcohol-impregnated wipe. Then, rigid cover 132 is carefully removed from the needle bundle assembly as illustrated in FIG. 3, exposing sheath 88 and sleeve 104.

The needle bundle assembly is then placed in the needle bundle holder 14. Sheath 88 is inserted through opening 142 in spring 44; and male index 144 on sheath 88 is engaged both laterally and rotationally with female index 146 on the outer surface of core 111 of plug 140. Bottom pod 118 is placed in channel 66.

Handles 48, 50 are then released from lock slots 74 whereupon the lock arm 46 drops downwardly to its rest position. This brings the clamping block 52 generally propinquant top pod 116. Clamping block 52 is then slid along handles 48, 50 until its concave arcuate face 124 is positioned directly above top pod 116.

Lock arm 46 is then forced downwardly, placing positive and substantial clamping force on clamping block 52 and bringing concave arcuate face 124 of the clamping block into firm engagement with arcuate top 120 of top pod 116. With the clamping force thus empowered, handles 48, 50 are then locked in lower lock slots 76, thus clamping the needle bundle between clamping block 52 (arcuate face 124) and support block 58 (channel 66).

The clamping force expressed between clamping block 52 and support block 58 is sufficient to hold the needle bundle in the position shown in FIGS. 5 and 6 through the process of driving the ends 98 of needles 84 into the tank 22; and until handles 48, 50 are released from lower lock slots 76. With the clamping force thus engaged at lock slots 76, through handles 48, 50, grooves 56 on the handles dig into the hard, but resiliently deformable polyethylene of sots 54, and the grooves 68 of channel 66 cooperate with bottom pod 118, to increase the hold of the needle bundle holder 14 on the needle bundle assembly 76 (minus rigid cover 132).

The combination of the needle bundle driver 10 and the needle bundle assembly 76 as shown in FIG. 5 comprises a needle bundle driver assembly. While only two needles are illustrated in FIGS. 4, 5, and 6, it is understood that the desired number of needles in the array can be selected to provide adequate fluid transfer capacity for the amount of fluid to be transferred. In the illustrated embodiment, the inventor contemplates e.g. 12 needles, 13 gauge in size. (Sleeve 104 has been omitted in FIGS. 5 and 6 to simplify the illustration.)

With the needle bundle firmly clamped in the needle holder 14 as shown in FIG. 5, rigid cover 130 is then removed and a tube 128 or like fluid carrier is coupled to coupling 126.

With indexes 144 and 146 engaged, each needle guide 94 in the sheath 88 is abutted against a corresponding needle channel 148 in the plug 140, through tape 110 on sheath 88, and corresponding tape 150 on the plug. Thus the engaging of indexes 144 and 146 assures that the sheath 88 is aligned, both rotationally and laterally with the plug, whereby each needle 84 is aligned with a needle channel 148 in the plug.

Power ram 16 is then activated, withdrawing ram arm 32, as coupled with guide plate 34. This moves the entire needle bundle assembly, including the needle bundle with its needles, toward the tank 22, driving the ends of the needles through tapes 110 and 150, through the needle channels 148 in plug 140, and into the interior of the tank, as shown in FIG. 6.

The needle ends may all protrude the same distance inside the tank wall, as illustrated in FIG. 6, and also as shown in FIG. 16 of my U.S. Pat. No. 4,941,517. In the alternative, the ends of the needles may be staggered as shown in FIG. 24 of U.S. Pat. No. 4,941,517, whereby the needles penetrate different distances inwardly from the inside surface of the tank wall after the needle bundle has been driven. In the instance of the staggered needles, the different length needles penetrate the tank wall at different moments, though normally all the needles do penetrate the tank in the same operation of driving the needle bundle.

Fluid, such as e.g. water or other liquid is then urged from tube 128, through the needles 84 and into the tank. So long as the plug 140 is immersed in fluid 152 inside the tank 22, as shown in FIG. 8, the needles, in the driven position shown in FIG. 6, can similarly be used to transfer fluid out of the tank.

When the fluid transfer has been completed, power ram 16 is again activated, extending ram arm 32. This moves guide plate 34 away from tank 22, thereby withdrawing the needle ends from tank 22 and the plug 140, and back into sheath 88. Tube 128 is then released from the needle bundle. Handles 48, 50 are then released from lower lock slots 76, are raised, and re-locked in lock slots 74 as shown in FIG. 1, thus unclamping the needle bundle.

The used needle bundle can then be removed from the needle holder 14 and returned to the lab for cleaning, re-sterilization, and any other preparation for re-use. After processing has been completed in tank 22, plug 140 is removed, and replaced with a new plug in preparation for the next use of the tank.

In the typical use contemplated herein, the needle bundle driver 10 is used to effect transfer of fluids into or out of a given tank during only a very small portion of the overall time during which the tank is actually in use. By corollary, for the vast majority of the time when the tank is in use, the needle bundle driver is not being used on that tank. Further, the needle bundle driver is a sensitive piece of equipment that can be damaged if left mounted on the tank and unprotected. Accordingly, the needle bundle driver is preferably kept in safe storage when it is not needed for use on any particular tank.

In preferred use, a single needle bundle driver 10 is used to service the fluid transfer operations in all of the tanks in a user's plant, recognizing that any given plant can include a variety of tank wall constructions. Specifically, different tanks have different wall thicknesses, depending on the use of the particular tank. Wall structure typically depends on such factors as e.g. strength requirements, insulation, heating or cooling fluids to be carried in the tank wall, etc.

It is contemplated that the thickness of the fluid receiver assembly 136 is to be constant. Since the adapter 138 and the plug 140 are positioned relative to the inner surface 170 of the wall 21, the position of the outer surface of the plug (e.g. tape 150) is determined relative to the inner surface 170 of the tank wall 21, and is generally insensitive to the thickness of the wall 21.

The positioning of the mounting base 24 is, however, controlled by the outer surface 172 of wall 21, against which mounting base 24 is positioned. Thus, the distance between support block 58 and plug 140 (e.g. tape 150) is variable from tank to tank, and depends at least in part on the thickness of tank wall 21.

Needle bundle driver 10 accommodates the variable distance between support block 58 and plug 140 by providing a lower clamping surface anywhere along the channel 66, with the clamping block 52 being able to slide along handles 48, 50, to provide the corresponding, and opposing, upper clamping surface. Thus, one needle bundle driver 10 can generally accommodate the different tank wall thickness encountered in most factories.

With ram arm 32 extended as shown in FIG. 5, the interfaces 144, 146 are engaged without consideration for where that puts bottom pod 118 along the length of support block 58, because channel 66 extends the necessary length of the support block to accommodate all tanks on which the needle bundle driver 10 is to be used. Similarly, the limits of the sliding range of clamping block 52, between lock rods 70, 72 and spring 44 are such as to accommodate all such tanks contemplated. Thus the ability to position the needle bundle anywhere along channel 66, and to correspondingly place clamping block 52 over top pod 116, gives a respective needle bundle driver 10 the versatility to service a plurality of tanks having different wall thicknesses, limited primarily by the length of channel 66 and the corresponding sliding range of clamping block 52. Typically, the needle bundle driver can accommodate differences in wall thickness of at least 4 inches, preferably at least 8 inches, and in some embodiments up to about 12 inches.

As referred to herein, "microbiological invasion" refers to invasion by living organisms such as bacteria, viruses, and the like. Further it refers to maintaining aseptic conditions, as opposed to sterile conditions.

Also as referred to herein "permanent" securement of an element to e.g. the tank means that the element is not removable without penetration of the tank or destruction of the element.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

What is claimed is:

1. A method of aseptically adding fluid to a closed tank, said method comprising the steps of:
   (a) securing a fluid receiver assembly in said wall of said tank, said fluid receiver assembly comprising a plug extending from the outside of the tank to the inside of the tank, said plug comprising needle channels adapted to convey needles from the outside of the tank toward the inside of the tank;
   (b) mounting a needle bundle in a needle bundle driver propinquant said fluid receiver assembly, to thereby make a needle bundle driver assembly, said needle bundle driver comprising (i) a tank bracket mounted adjacent said tank, said tank bracket having first and second ends facing toward and away from said tank, respectively, (ii) a needle bundle holder mounted to said tank bracket and moveable on said tank bracket, toward and away from said first end of said tank bracket, and (iii) a power ram secured to said tank bracket and adapted to move said needle bundle holder toward, and away from, said first end of said tank bracket;
   said needle bundle comprising (i) a needle holder, said needle holder having first and second ends, (ii) a plurality of needles extending from said first ends of said needle holder, to ends of said plurality of needles, (iii) a sheath covering said ends of said plurality of needles, and (iv) a spring disposed against said first end of said needle holder, and positioning said sheath with respect to said plurality of needles, said mounting of said needles bundle in said needle bundle driver including the step of removing said needle bundle cover;
   (c) engaging a first index on said needle bundle with a second cooperating index on a plug;
   (d) immobilizing said needle bundle in said needle bundle driver;
   (e) after step (d), connecting an aseptic fluid carrier to said second end of said needle holder;
   (f) after step (e), driving said needle bundle driver assembly toward said tank, whereby said ends of said plurality of needles pass through said plug and into said tank, thereby establishing fluid communication with the interior of said tank; and
   (g) passing fluid through said plurality of needles between said aseptic fluid carrier and said closed tank.

2. A method of driving needles aseptically into a closed tank through a plug, mounted in a wall of said tank, said plug extending through said wall, said method comprising the steps of:
   (a) releasably mounting a needle bundle driver to said tank, through a mounting base, at least a portion of said mounting base being permanently secured to said tank;
   (b) securing a needle bundle in said needle bundle driver, said needle bundle comprising a needle holder, and a plurality of needles in said needle holder, said plurality of needles having ends disposed toward said plug, said plurality of needles being aligned with needle channels in said plug;
   (c) driving said plurality of needles into said plug such that said ends of said plurality of needles project through said plug and into said tank, whereby fluid can be passed aseptically through said plurality of needles between said needle holder and said tank;
   (d) passing fluid through said plurality of needles between said needle holder and said tank;
   (e) withdrawing said plurality of needles from said plug;
   (f) releasing and removing said needle bundle from said needle bundle driver; and
   (g) dismounting said needle bundle driver from said tank while leaving said mounting base mounted to said tank.

3. A method of aseptically transferring fluid into a plurality of tanks, said method comprising the steps of:
   (a) securing a mounting base to each of said plurality of tanks, at least a portion of each said mounting base being permanently secured to the respective said tank;
   (b) securing a fluid receiver assembly to a wall in each of said plurality of tanks such that said fluid receiver assembly extends through the respective said wall in each said tank, said fluid receiver assembly comprising a tank adapter permanently secured into the wall of the respective said tank, and a plug in said adapter, said plug extending through the wall of the tank, and having needle channels adapted to receive needles passing through said plug and into the respective said tank;

(c) mounting a needle bundle driver to said mounting base on a first one of said plurality of tanks, mounting a first needle bundle, having a first needle holder, and a first plurality of needles extending from said first needle holder, driving said first plurality of needle into said first tank, and transferring fluid through said first plurality of needles between said first needle holder and said first tank;

(d) removing said first plurality of needles from said first tank, removing said first needle bundle from said needle bundle driver, and removing said needle bundle driver from said first tank;

(e) mounting said needle bundle driver to said mounting base on a second one of said plurality of tanks; mounting a second needle bundle, having a second needle holder, and a second plurality of needles, extending from said second needle holder, driving said second plurality of needles into said second tank, and transferring fluid through said second plurality of needles between said second needle holder and said second tank.

4. A method of driving ends of a plurality of needles aseptically through a wall of a closed tank, and thus into said tank, said method comprising the steps of:

(a) securing a fluid receiver assembly in said wall of said tank, said fluid receiver assembly comprising a plug extending from the outside of the tank to the inside of the tank, said plug comprising needle channels adapted to convey needles from the outside of the tank toward the inside of the tank;

(b) mounting a needle bundle in a needle bundle driver propinquant said fluid receiver assembly, to thereby make a needle bundle driver assembly, said needle bundle driver comprising (i) a tank bracket mounted adjacent said tank, said tank bracket having first and second ends facing toward and away from said tank, respectively, (ii) a needle bundle holder mounted to said tank bracket and moveable on said tank bracket, toward and away from said first end of said tank bracket, and (iii) a power ram secured to said tank bracket and adapted to move said needle bundle holder toward, and away from, said first end of said tank bracket;

said needle bundle comprising (i) a needle holder, said needle holder having first and second ends, (ii) a plurality of needles extending from said first end of said needle holder, to ends of said plurality of needles, (iii) a sheath covering said ends of said plurality of needles, and (iv) a spring disposed against said first end of said needle holder, and positioning said sheath with respect to said plurality of needles;

(c) engaging a first index on said needle bundle with a second cooperating index on said plug;

(d) immobilizing said needle bundle in said needle bundle driver; and (e) driving said needle bundle toward said tank, whereby said ends of said plurality of needles pass through said plug and into said tank, thereby establishing fluid communication with the interior of said tank.

5. A needle bundle driver, adapted to drive needles in a bundle through an aseptic tank plug mounted in a wall of a tank, such that ends of the needles project into the tank, whereby the needles provide aseptic fluid communication through the wall of the tank, said needle bundle driver comprising:

(a) a tank bracket adapted to mount said needle bundle driver adjacent the tank, said tank bracket having a first end defined by a first end plate adapted to face toward the tank, a second end defined by a second end plate adapted to face away from the tank, and a length between said first and second ends;

(b) a needle bundle holder mounted to said tank bracket and moveable, along the length of said tank bracket, toward and away from said first end of said tank bracket, said needle bundle holder comprising (i) a support block, said support block having first and second ends disposed respectively toward said first and second ends of said tank bracket, a top, and a recess in said top, (ii) a lock arm, said lock arm having first and second ends disposed toward said first and second ends respectively of said support block, said lock arm being mounted above said support block by a web, mounting said lock arm for angular movement with respect to said first end of said support block, whereby said second end of said lock arm can be raised or lowered while said first end of said lock arm remains at a relatively constant height above said support block, (iii) an upper lock adapted to lock said second end of said lock arm in a raised position, (iv) a lower lock adapted to lock said second end of said lock arm in a lowered position, and (v) a clamping block mounted to said lock arm; and (c) as power ram secured to said tank bracket and adapted to move said needle bundle holder toward, and away from, said first end of said tank bracket.

6. A needle bundle driver as in claim 5 wherein said web comprises a spring, biasing said lock arm for angular movement with respect to said first end of said support block, said second end of said lock arm, as supported by said spring through said first end of said lock arm, having a rest position between said first raised position and said second lowered position.

7. A needle bundle driver as in claim 5 wherein said clamping block is slidably mounted to said lock arm, such that said clamping block can slide, along said lock arm, toward and away from said first end of said lock arm.

8. A needle bundle driver as in claim 7, said lock arm being received in a slot in said clamping block whereby said slot and said lock arm are engaged to effect said sliding of said lock arm with respect to said clamping block, said lock arm having a plurality of grooves therein, at least 0.25 millimeter deep, extending across the direction of sliding of said clamping block such that said grooves pass through said slot in said clamping block as said clamping block slides with respect to said lock arm.

9. A needle bundle driver as in claim 5, said clamping block having an arcuate face disposed toward said support block.

10. A needle bundle driver as in claim 5, said recess in said top of said support block comprising a channel, said channel having a length, extending between said first and second ends.

11. A needle bundle driver as in claim 10, said channel having a plurality of grooves therein, at least 0.25 millimeter deep, extending across said channel, in a direction transverse to said length.

12. An assembly, comprising:
(a) a needle bundle driver, adapted to drive needles in a bundle through an aseptic tank plug mounted in a wall of a tank, such that ends of the needles project into the tank, whereby the needles provide aseptic fluid communication through the wall of the tank, said needle bundle driver comprising (i) a tank bracket adapted to mount said needle bundle driver adjacent the tank, said tank bracket having a first end adapted to face toward the tank, a second end adapted to face away from the tank, and a length between said first and second ends, (ii) a needle bundle holder mounted to said tank bracket and moveable along the length of said tank bracket, toward and away from said first end of said tank bracket, said needle bundle holder comprising (aa) a support block, said support block having first and second ends disposed respectively toward said first and second ends of said tank bracket, a top, and a recess in said top, (bb) a lock arm, said lock arm having first and second ends disposed toward said first and second ends respectively of said support block, said lock arm being mounted above said support block by a lock arm support, mounting said lock arm for angular movement with respect to said first end of said support block, whereby said second end of said lock arm can be raised or lowered while said first end of said lock arm remains at a relatively constant height above said support block, (cc) a lock adapted to lock said second end of said lock arm in a lowered position, and (dd) a clamping block mounted to said lock arm; and (iii) a power ram adapted to move said needle bundle holder toward, and away from, said first end of said tank bracket; and
(b) a needle bundle comprising (i) a needle holder, said needle holder having first and second ends, (ii) a plurality of needles extending from said first end of said needle holder to ends of said plurality of needles, said plurality of needles being arranged, as an array, in a pattern, (iii) a sheath, having a first end disposed away from said needle holder and a second end disposed toward said needle holder, needle guides in said sheath, aligned with said first and second ends of said sheath, said needle guides being arranged in the same pattern as said plurality of needles, said sheath being disposed over said ends of said plurality of needles, and (iv) a spring disposed between said needle holder and said sheath, and positioning said sheath such that said ends of said plurality of needles are disposed in said sheath,
said needle bundle being securely held in said needle bundle driver.

13. An assembly as in claim 12, said assembly having a longitudinal axis, said plurality of needles extending along said longitudinal axis, said needle holder comprising a pair of clamp arms extending to ends thereof, in a direction transverse to said longitudinal axis, and top and bottom pods on said ends of respective ones of said clamp arms, said top and bottom pods having respective ends, said clamping block having an arcuate face disposed toward said support block, said top and bottom pods being engaged with, and clamped between, said arcuate face in said clamping block and said recess in said support block, respectively.

14. A needle bundle driver assembly as in claim 13 wherein said arcuate face in said clamping block generally corresponds in shape with the shape of said end of said top pod, and wherein said recess in said support block generally corresponds, in a direction transverse to said longitudinal axis, with the shape of said ends of said bottom pod.

15. An assembly as in claim 12, further comprising an aseptic transfer system, said system including a plug, mounted in a wall of a tank, and adapted to accommodate aseptic penetration of needles therethrough, to thereby facilitate aseptic fluid communication through said plurality of needles, between the tank and said needle holder, said plug and said sheath having cooperating index guides, such that said index guides cooperate with each other only when said plurality of needles in said needle bundle are both laterally and rotationally aligned with corresponding needle channels in said plug.

16. An assembly as in claim 15, said plurality of needles extending along a longitudinal axis of said assembly, said needle holder comprising a pair of clamp arms extending to ends thereof, in a direction transverse to said longitudinal axis, and top and bottom pods on said ends of respective ones of said clamp arms, said top and bottom pods having respective ends, said clamping block having an arcuate face disposed toward said support block, said ends of said top and bottom pods being engaged with, and clamped between, said arcuate face in said clamping block and said recess in said support block, respectively.

17. An assembly as in claim 16 wherein said arcuate face in said clamping block generally corresponds in shape with the shape of said end of said top pod, and wherein said recess in said support block generally corresponds, in a direction transverse to said longitudinal axis, with the shape of said end of said bottom pod.

18. A needle bundle driver, adapted to drive needles in a bundle through an aseptic tank plug mounted in a wall of a tank, such that ends of the needles project into the tank, whereby the needles provide aseptic fluid communication through the wall of the tank, said needle bundle driver comprising:
(a) a tank bracket adapted to mount said needle bundle driver adjacent the tank, said tank bracket having a first end adapted to face toward the tank, a second end adapted to face away from the tank, and a length between said first and second ends;
(b) a needle bundle holder mounted to said tank bracket and moveable, along the length of said tank bracket, toward and away from said first end of said tank bracket, said needle bundle holder comprising (i) a support block, said support block having first and second ends disposed respectively toward said first and second ends of said tank bracket, a top, and a recess in said top, (ii) a lock arm, said lock arm having first and second ends disposed toward said first and second ends respectively of said support block, said lock arm being mounted above said support block by a lock arm support, mounting said lock arm for angular movement with respect to said first end of said support block, whereby said second end of said lock arm can be raised or lowered while said first end of said lock arm remains at a relatively constant height above said support block, (iii) lock adapted to lock said second end of said lock arm in a lowered position, and (iv) a clamping block mounted to said lock arm; and (c) as power ram secured to said tank bracket and adapted to move said needle bundle holder toward, and away from, said first end of said tank bracket.

19. A needle bundle driver as in claim 18 wherein said lock arm support comprises a spring, biasing said lock arm for angular movement with respect to said first end of said support block, said second end of said lock arm, as supported by said spring through said first end of said lock arm, having a rest position above said lowered position.

20. A needle bundle driver as in claim 18 wherein said clamping block is slidably mounted to said lock arm, such that said clamping block can slide, along said lock arm, toward and away from said first end of said lock arm.

21. A needle bundle driver as in claim 20, said lock arm being received in a slot in said clamping block whereby said slot and said lock arm are engaged to effect said sliding of said lock arm with respect to said clamping block, said lock arm having a plurality of grooves therein, at least 0.25 millimeter deep, extending across the direction of sliding of said clamping block such that said grooves pass through said slot in said clamping block as said clamping block slides with respect to said lock arm.

22. A needle bundle driver as in claim 14, said clamping block having an arcuate face disposed toward said support block.

23. A needle bundle driver as in claim 18, said recess in said top of said support block comprising a channel, said channel having a length, extending between said first and second ends.

24. A needle bundle driver as in claim 23, said channel having a plurality of grooves therein, at least 0.25 millimeter deep, extending across said channel, in a direction transverse to said length.

* * * * *